(12) United States Patent
Awaad et al.

(10) Patent No.: US 9,192,639 B1
(45) Date of Patent: Nov. 24, 2015

(54) CONVOLVULUS EXTRACT FOR TREATMENT OF PEPTIC ULCER AND HELICOBACTER PYLORI INFECTION

(71) Applicant: KING SAUD UNIVERSITY, Riyadh (SA)

(72) Inventors: Amani S. Awaad, Riyadh (SA); Asma'a Al-Rifai, Riyadh (SA); Reham M. El-Meligy, Riyadh (SA); Mohamed E. Zain, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/497,265

(22) Filed: Sep. 25, 2014

(51) Int. Cl.
  *A61K 36/00* (2006.01)
  *A61K 36/39* (2006.01)
  *A61K 31/235* (2006.01)

(52) U.S. Cl.
  CPC ............... *A61K 36/39* (2013.01); *A61K 31/235* (2013.01)

(58) Field of Classification Search
  CPC ..................................................... A61K 36/39
  See application file for complete search history.

(56) References Cited

U.S. PATENT DOCUMENTS 6,083,510 A   7/2000  Meng et al.

OTHER PUBLICATIONS

Vimal et al. (2010) PHCOGJ vol. 2, Issue 11, pp. 436-441.*
Alqasoumi (Thesis) May 13, 2007. pp. 108-110.*
Revilla et al. (1998) J. Agric. Food Chem. 46, 4596-4597.*
Sharath et al. (2015) World Journal of Pharmacy and Pharmaceutical Sciences vol. 4, Issue 02, 498-507.*

* cited by examiner

*Primary Examiner* — Chris R Tate
*Assistant Examiner* — Russell Fiebig
(74) *Attorney, Agent, or Firm* — Richard C. Litman

(57) ABSTRACT

The *Convolvulus* extract for treating peptic ulcer and *Helicobacter pylori* infection is an ethanolic extract from *C. pilosellifolius*. The extract is prepared by homogenizing *Convolvulus pilosellifolius* aerial plant parts to prepare a powder, percolating the powder with an organic solvent to prepare a suspension, filtering the suspension to obtain a filtrate, and obtaining the extract as a dry powder by drying the solvent under reduced pressure from the filtrate. The active ingredient in the extract is a compound that was isolated from the extract of *C. pilosellifolius* as a purified triterpene using silica gel column chromatography, the compound being named: 2-propoxyethyl 13-(4-ethoxy-4-oxobutyl)-6b,8a12b,14a-tetramethyl-5,6,6a,6b,7,8,8a,9,10,11,12,12a,12b,14a-tetradecahydropicene-2-carboxylate. Both the extract and the isolated active ingredient exhibit anti-ulcerogenic activity, and disk diffusion tests show that various strains of *H. pylori* are susceptible to both the extract and the active ingredient.

8 Claims, No Drawings

CONVOLVULUS EXTRACT FOR TREATMENT OF PEPTIC ULCER AND HELICOBACTER PYLORI INFECTION

BACKGROUND OF THE INVENTION

1. Field of the Invention

The present invention relates to purified plant extracts effective against peptic ulcer, and particularly to a *Convolvulus* extract for the treatment of peptic ulcer and *Helicobacter pylori* infection that is an extract of *Convolvulus pilosellifolius*, and to the active ingredient isolated from the extract.

2. Description of the Related Art

The family Convolvulaceae contains a large number of plants. The largest genus is *Convolvulus*, which comprises about 250 species of flowering plants, including trees, shrubs and herbs. Common names include bindweed and morning glory, both names shared with other closely related genera. They are annual or perennial herbaceous vines, bines and a few species of woody shrubs that grow from 0.3 to 3 meters tall. The leaves are spirally arranged and the flowers trumpet-shaped, mostly white or pink, but may occur as blue, violet, purple or yellow in some species. *Convolvulus pilosellifolius*, a species of *Convolvulus*, is commonly known as soft bindweed. Most of the *Convolvulus* plants contain alkaloids, flavonoids and coumarins. In addition, they possess many pharmacological properties, including cytotoxic, antioxidant, anti-inflammatory and antiulcer activities. Some *Convolvulus* plants are used in traditional medicine (TM) for the treatment of coughs and asthma.

Peptic ulcer is a common gastrointestinal disorder in the modern era, and it is a global health problem affecting a large number of people worldwide. *Helicobacter pylorus* is recognized as a major etiologic agent in gastrodudenal diseases, including chronic gastritis, peptic ulcers, gastric adenocarcinoma and mucosa-associated lymphoid tissue lymphoma. The current treatment regimens for *H. pylori* infections are based on the combination of a proton pump inhibitor and two antibiotics (triple therapy). There are different classes of drugs that have been used in the treatment of peptic ulcer. Most of them, however, exhibit serious side effects, such as arrhythmias, gynaecomastia, arthralgia and hypergastrinemia. Additionally, the use of antibiotics leads to increasing development of bacterial resistance that has compromised the efficacy of this method of treatment.

Increasing antibiotic resistance in clinical isolates of bacteria, including *H. pylori*, strongly support the search for new and safe antibacterial compounds from native medicinal plants. In this regard, many species of plant and their derivatives, including isolated compounds and extracts of the lichen *Certaria islandica*, Chinese green tea and several native plants used in folk medicine for the relief of gastric symptoms have been studied to establish their pharmacological activity. In fact, a number of drugs and natural substances, such as various essential oils, extracts of the lichen *Certaria islandica*, Chinese green tea and several native Iranian plants have been shown to have in vitro antibacterial activity against *H. pylori*. There are also some published studies on the activity of a number of plant extracts against *Helicobacter pylori*.

Therefore, in the discovery of new anti-ulcerogenic drugs, special interest has been directed to natural plant products based upon traditional medicine (TM). Therapies based on natural products (plants & herbs) derived from TM have proved to be clinically effective and relatively less toxic than the existing pharmaceutical drugs because it reduces the offensive side effects of pharmaceutical drugs, especially those caused by *Helicobacter pylori*. Accordingly, the search for new effective therapeutic agents is of paramount importance to find more effective natural product, pure extracts and active compounds derived from TM that are effective against ulcer activity caused by *Helicobacter pylori*.

Thus, a *Convolvulus* extract for treating peptic ulcer and *Helicobacter pylori* infection solving the aforementioned problems is desired.

SUMMARY OF THE INVENTION

The *Convolvulus* extract for treating peptic ulcer and *Helicobacter pylori* infection is an ethanolic extract from *C. pilosellifolius*. The extract is prepared by homogenizing *Convolvulus pilosellifolius* aerial plant parts to prepare a powder, percolating the powder with an organic solvent to prepare a suspension, filtering the suspension to obtain a filtrate, and obtaining the extract as a dry powder by drying the solvent under reduced pressure from the filtrate. The active ingredient in the extract is a compound that was isolated from the extract of *C. pilosellifolius* as a purified triterpene using silica gel column chromatography, the compound being named: 2-propoxyethyl 13-(4-ethoxy-4-oxobutyl)-6b,8a12b,14a-tetramethyl-5,6,6a,6b,7,8,8a,9,10,11,12,12a,12b,14a-tetradecahydropicene-2-carboxylate having the following structural formula:

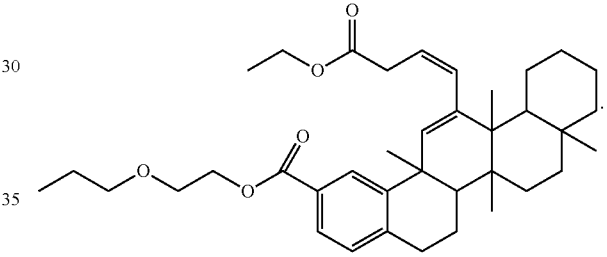

A method of treating peptic ulcer is provided, which includes administering an extract of *C. pilosellifolius* or the compound of the above formula to a mammal in need thereof in an amount effective to reduce or inhibit ulcer activity and gastrointestinal disorders (chronic gastritis, ulcers, gastric adenocarcinoma and mucosa-associated lymphoid tissue lymphoma) caused by bacterium *Helicobacter pylori*.

Surprisingly, the extract from *C. pilosellifolius* and the isolated and purified active compound of formula shown above were discovered to inhibit peptic ulcers and gastric disorders resulting from *Helicobacter pylori* infection in a subject mammal.

These and other features of the present invention will become readily apparent upon further review of the following specification.

DETAILED DESCRIPTION OF THE PREFERRED EMBODIMENTS

The *Convolvulus* extract for treating peptic ulcer and *Helicobacter pylori* infection is an ethanolic extract from *C. pilosellifolius*. The extract is prepared by homogenizing *Convolvulus pilosellifolius* aerial plant parts to prepare a powder, percolating the powder with an organic solvent to prepare a suspension, filtering the suspension to obtain a filtrate, and obtaining the extract as a dry powder by drying the solvent under reduced pressure from the filtrate. The active ingredient in the extract is a compound that was isolated from the extract of *C. pilosellifolius* as a purified triterpene using silica gel column chromatography, the compound being named: 2-propoxyethyl 13-(4-ethoxy-4-oxobutyl)-6b,8a12b,14a-tetramethyl-5,6,6a,6b,7,8,8a,9,10,11,12a,12b,14a-tetradecahydropicene-2-carboxylate having the following structural formula:

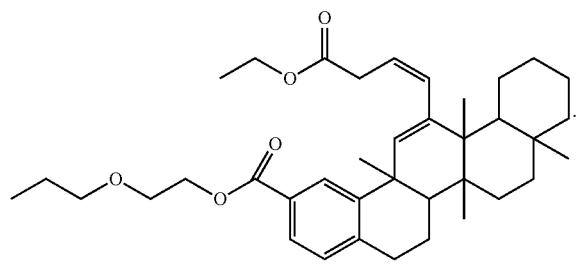 [SMILES: CCCOCCOC(=O)c1ccc2c(c1)C1(C)C=C(/C=C\CC(=O)OCC)C3(C)C4CCCCC4(C)CCC3(C)C1CC2]

A method of treating peptic ulcer is provided, which comprises administering an extract of C. pilosellifolius to a mammal in need thereof in an amount effective to inhibit ulcer activity caused by bacterium Helicobacter pylori. The extract is prepared by homogenizing Convolvulus pilosellifolius aerial plant parts to prepare a powder, percolating the powder with an organic solvent to prepare a suspension, filtering the suspension to obtain a filtrate, and isolating the extract by drying the solvent under reduced pressure from the filtrate. The active ingredient of the above formula is obtained by dispersing the dry extract in water to remove any water soluble compounds, filtering the lipid layer from the aqueous dispersion, dissolving the lipid layer in chloroform, drying the dissolved lipid layer with sodium sulfate, concentrating the dissolved lipid layer at reduced pressure to form a dry extract, eluting the dry extract through a chromatography column with a hexane:ethyl acetate eluent, collecting the fraction of the eluent that is pale yellow in color, and crystallizing the pale yellow eluent to obtain the active ingredient. The active ingredient may also be used, by itself, to treat peptic ulcers and Helicobacter pylori infections.

Example 1

Isolation of Active Ingredient

The air-dried powder of 1000 g of C. pilosellifolius (aerial parts) was extracted using ethanol (95%) in a Soxhlet apparatus until complete exhaustion. The total ethanol extract was concentrated under reduced pressure at a temperature not exceeding 35° C. to yield a dry extract of 260 g.

The ethanol extract, about 240 g, was dispersed in 600 ml of distilled water and filtered using cotton piece to separate a lipid layer from other contents in an aqueous layer. The lipid layer was dissolved in chloroform, dried over anhydrous sodium sulfate, and concentrated under reduced pressure at a temperature not exceeding 35° C. to yield about 86 g of dry extract. The residue obtained was re-applied on a column packed with silica gel and eluted with hexane-ethyl acetate (95:5), from which compound A1 was isolated, Compound A1: (30 mg), pale yellow color, 0.86 in hexane-ethyl acetate (86:14), melting point: 214-216° C. $^1$H NMR (CDCl$_3$): δ 7.95 (δ 1.01-1.89 (1H, m, H-1-13); δ 2.29 (1H, d, J=9.85 Hz, H-16); δ 2.29 (t, 9.85, H-27); δ 4.14 (q, 8.05 H-34); δ 4.24 (t, H-36); 4.29 (t, H-35); δ 4.32 (t, H-34); δ 8.11 (1H, S, H-19); δ 7.72 (1H, d, J=2.8 Hz, H-21); δ 7.54 (1H, d, J=2.8 Hz, H-22). $^{13}$C NMR (CDCl$_3$): δ 34.39 (C−1), 39.37 (C-2), 38.74 (C-3), 29.36 (C-4), 30.36 (C-5), 28.98 (C-6), 38.91 (C-7), 30.61 (C-8), 130.86 (C-9), 132.46 (C-10), 22.69 (C-11), 24.99 (C-12), 23.96 (C-13), 31.92 (C-14), 31.92 (C-15),19.15 (C-16), 29.15 (C-17), 128.79 (C-18), 129.98 (C-19), 128.84 (C-20), 128.85 (C-21), 129.47 (C-22), 129.74 (C-23), 19.18 (C-24), 19.74 (C-25), 29.27 (C-26), 28.93 (C-27), 29.59 (C-28), 22.96 (C-29), 29.46 (C-30), 173.92 (C-31), 60.13 (C-32), 14.24 (C-33), 167.74 (C-34), 65.55 (C-35), 67.75 (C-36), 68.13 (C-37), 23.75 (C-38), 14.11 (C-39).

The isolated compound A1 was named as 2-propoxyethyl 13-(4-ethoxy-4-oxobutyl)-6b,8a,12b,14a-tetramethyl-5,6,6a,6b,7,8,8a,9,10,11,12,12a,12b,14a-tetradecahydropicene-2-carboxylate, having the following structure:

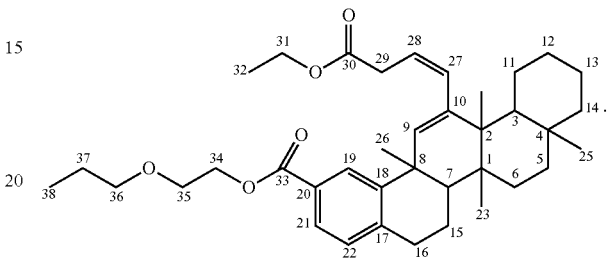

Example 2

Preparation of Extract for Biological Testing

An extract of C. pilosellifolius was prepared according to the following procedure. The aerial parts of C. pilosellifolius were collected during flowering stage, and these parts were air dried in shade, homogenized and reduced to fine powder and kept for phytochemical and biological investigation. The dried aerial parts of C. pilosellifolius (100 g) were extracted by percolation in 90% ethanol at room temperature for two days in a Soxhlet apparatus. The ethanol extract was filtered and the residues were re-percolated for four times. The total ethanol extract was concentrated under reduced pressure at a temperature not exceeding 35° C. to yield a dry extract of 15 g. The dried extract was freshly suspended in distilled water just before administration in the following examples by the aid of Tween 80.

Example 3

Determination of Median Lethal Dose (LD$_{50}$)

Swiss albino mice of both sex (26-30 g) and male Wistar rats (180-200 g) were supplied by the animal house of King Saud University. Animals were housed in standard polypropylene cages with wire mesh top and maintained under standard conditions (temperature 23±1.0° C., humidity 55±10%, 12 h light/12 h dark cycle). The mice were fed with a standard pellet diet with water ad libitum and were allowed to adapt to the laboratory environment for one week before experimentation.

Swiss albino mice in groups of six received one of 500, 1000, 2000, or 4000 mg/kg doses of the tested extract. Control animals received the vehicle only and were kept under the same conditions. Signs of acute toxicity and the number of deaths per dose within 24 hours were recorded. The total alcohol extract of C. pilosellifolius did not produce any behavioral changes or mortality in treated mice in doses up to 4000 mg/kg. Therefore, the tested plant can be categorized as highly safe, since substances possessing LD$_{50}$ higher than 50 mg/kg are non-toxic.

Example 4

Anti-Ulcerogenic Activity

Evaluation of the anti-ulcerogenic activity was carried out using an absolute ethanol-induced ulcer model according to published methods. About 30 Wistar rats were divided into 5 groups, each of 6 rats. Group 1 received the vehicle and served as control group. Group 2 received ranitidine (100 mg/kg) and served as a standard group. Groups 3 and 4 received the total alcohol extract of the plant under investigation at doses 500 and 1000 mg/kg, respectively. Group 5 received the isolated compound A1 at doses of 50 mg/kg, respectively.

Rats of all groups were fasted for 24 hours, and then all medications were administered orally. One hour after treatment, the animals received an oral dose of absolute ethanol (1 ml/200 g), and were then sacrificed one hour later by ether inhalation. The stomachs were rapidly removed, opened along their greater curvature, and gently rinsed under running tap water. The number of lesions in the glandular part of the stomach was measured under an illuminated magnifying microscope (10×). Long lesions were counted and their lengths were measured. Petechial lesions were counted, and then each five petechial lesions were taken as 1 mm of ulcer. The mucosal lesions were quantified by the scoring system (0-5), where 0=no damage; 1=Local edema and inflammation without ulcers; 2=One ulcer without inflammation; 3=one to two ulcers with inflammation & lesion diameter <1 cm; 4=More than two ulcers with lesion diameter 1-2 cm; 5=Sever ulceration with lesion diameter >2 cm.

To calculate the ulcer index (mm), the sum of the total length of long ulcers and petechial lesions in each group of rats was divided by its number. The curative ratio was determined according to the formula:

% Protection of control ulcer=Control $UI$–Test $UI$/Control $UI$×100.

The results showed that the plant extract at doses of 500 and 1000 mg/kg possessed a potent anti-ulcerogenic activity against ulcer induced by absolute alcohol. It produced a percent protection of control ulcer by 69.2% and 84.6% respectively, which are more effective than ranitidine, which produce about 46.2%. The lipoidal layer showed significant anti-ulcerogenic activity of 78.5%. The isolated compound A1 (50 mg/kg), showed the highest activity of 95.4%, and it was mainly responsible for the activity of the investigated plant, as shown in Table 1.

TABLE 1

Anti-ulcerogenic effect of extract and compound A1 isolated from *C. pilosellifolius*

| Groups | Dose (mg/kg) | Score | No. of Ulcers | Ulcer Index | % Protection |
|---|---|---|---|---|---|
| Control | — | 4 | 14 ± 2.3 | 13 ± 2.24 | 0 |
| Ranitidine | 100 | 2.2 | 7.2*** ± 0.84 | 7** ± 1.58 | 46.2 |
| Total alcohol extract | 500 | 0.8 | 2.2*** ± 1.64 | 4*** ± 1.58 | 69.2 |
| Total alcohol extract | 1000 | 0.4 | 0.4*** ± 0.55 | 2***1.41 | 84.6 |
| Lipid 250 | 250 | 2 | 1.8*** ± 0.84 | 2.8*** ± 1.3 | 78.5 |
| Compound A1 | 50 | 1 | 0.6*** ± 0.55 | 0.6*** ± 0.5 | 95.4 |

Data are expressed as mean ± SD, n = 6, *p ≤ 0.05, p ≤ 0.01, *p ≤ 0.001

Example 5

Effect on Liver and Kidney Functions

Male Wister rats were divided into 2 equal groups of 10 rats each. The first group was left as a control and administrated water orally, while the second group was orally given the plant extracts in a dose of 1000 mg/kg for 15 days. Blood samples were collected from the orbital plexus of the rats 6 hours after the last dose. Samples were left to clot at room temperature for 30 minutes, and then centrifuged at 1000 rpm for 20 minutes. The collected sera were used for determination of the activity of both aspirate aminotransferase (AST) and alanine aminotransferase (ALT) as liver markers. In addition, levels of blood urea and serum creatinine were also estimated as kidney markers.

The investigated extract showed no alteration in both liver and kidney functions after 2 weeks of administration of 1000 mg/kg, as shown in Table 2.

TABLE 2

Effect of *C. pilosellifolius* extract on liver and kidney functions of rats

| Groups | ALT (U/l) | AST (U/l) | Blood Urea (mg/dl) | Serum Creatinine (mg/dl) |
|---|---|---|---|---|
| Control | 4.84 ± 0.35 | 5.20 ± 0.27 | 45.50 ± 1.26 | 0.82 ± 0.03 |
| *C. pilosellifolius* extract (1000 mg/kg) | 4.90 ± 0.22 | 5.15 ± 0.19 | 46.10 ± 1.5 | 0.83 ± 0.04 |

Data are expressed as mean ± SD, n = 10

These results showed that the alcohol extract of the investigated plant didn't reveal hepatotoxic manifestations. In addition, no apparent nephrotoxic manifestations were recorded. These result further indicated that no side effects were obtained from the alcohol extract of *C. pilosellifolius*.

Example 6

In-Vitro Anti-*Helicobacter pylori* Bacterial Activity

A total of seven clinical isolates of *Helicobacter pylori* were isolated from 19 biopsies received from patients diagnosed with gastritis or peptic ulcer disease. Clinical isolates were symbolized from KA1 to KA7. Isolates were grown in Brucella agar plates (Difco, Detroit, Mich., USA) containing 10% v/v sheep serum at 37° C. Identification was carried out using Gram stain and catalase, oxidase and urea hydrolysis activities. *H. pylorus* ATCC 43504 was used as control.

The disk diffusion test was used as screening to determine the susceptibility of *H. pylori* isolates and reference strain ATCC 43504 to plant extracts. The bacterial suspensions were spread-plated onto Brucella Agar plates (Difco, Detroit, USA) supplemented with 10% defibrinated sheep blood. Filter paper disks of 6 mm diameter impregnated with 5 mg of each extract (50 µl of stock solutions) were placed onto the surface of the inoculated agar. The plates were incubated at 37° C. under microaerophilic conditions and observed after 2 to 5 days.

The activity of the total alcohol extract and the compound A1 isolated from *C. pilosellifolius* against *Helicobacter pylori* was determined, as shown in Table 3. Seven isolates of *H. pylori* were obtained from 19 gastric biopsies, and their susceptibility to the total alcohol extract, two antibiotics, and the compound A1 isolated from *C. pilosellifolius* was determined by disc diffusion. The results are reported as the radius of the zone of inhibition of the bacterium in millimeters. All of the isolates of *H. pylori*, with the exception of isolate KA01 that was resistant to amoxicillin, were sensitive to the total alcohol extract, the isolated compound A1, amoxicillin and erythromycin.

TABLE 3

Activity of Total Alcohol Extract & Compound A1 Against Clinical Isolates of *H. pylori*

| H. pylori strains | Total alcohol extract (5 mg) | Compound A1 (5 mg) | Amoxicillin (30 μg) | Erythromycin (15 μg) |
|---|---|---|---|---|
| KA01 | 11 | 11 | R* | 19 |
| KA02 | 12 | 14 | 20 | 23 |
| KA03 | 9 | 10 | 21 | 22 |
| KA04 | 8 | 10 | 20 | 22 |
| KA05 | 14 | 17 | 22 | 20 |
| KA06 | 11 | 11 | 23 | 24 |
| KA07 | 13 | 12 | 25 | 23 |
| ATCC 43504 | 12 | 19 | 30 | 28 |

*R: Resistant

As shown in Table 3, the results revealed that the highest inhibition zones (19 and 17 mm) were obtained by the isolated compound against *H. pylori* strains ATCC 43504 and KA05, respectively. On the other hand, the lowest inhibition zones (8 and 9 mm) were obtained by the total alcoholic extract against *H. pylori* strains KA04, and KA03, respectively.

Example 7

Determination of the Minimum Inhibitory Concentration (MIC)

The determination of the minimum inhibitory concentration (MIC) was carried out by the broth micro dilution assay. A total of 100 μl of BHI broth supplemented with 10% defibrinated sheep blood inoculated with 6×10⁸ *Helicobacter pylori* (McFarland turbidity standard 2) and 100 μL of serial dilutions of HECb and BI dissolved in 2% Tween (v/v) was added to each well in the microplate to reach final concentrations of 25; 50; 100; 200; 400 and 800 μg/mL. The standard drug, Clarithromycin, was diluted to the same concentrations. The microplate was incubated at 37° C. under microaerophilic conditions in an atmosphere of 5-15% $O_2$ and 5-10% $CO_2$ for 48-72 hours. After incubation, the plates were visually examined. The optical density was determined at 450 nm, and each well was replicated in blood agar (Mueller-Hinton agar with 5% sheep blood) to determine the MIC.

The minimum inhibitory concentration (MIC) was determined for the total alcohol extract and the compound A1 isolated from *C. pilosellifolius* using the broth dilution method, as shown in Table 4.

TABLE 4

Minimum Inhibitory Concentration (MIC) of Total Alcohol Extract and Compound A1 Against Clinical Isolates of *H. pylori*

| H. pylori strains | Concentration Alcohol Extract (μg/mL) | Compound A (μg/mL) |
|---|---|---|
| KA01 | 200 | 100 |
| KA02 | 200 | 50 |

TABLE 4-continued

Minimum Inhibitory Concentration (MIC) of Total Alcohol Extract and Compound A1 Against Clinical Isolates of *H. pylori*

| H. pylori strains | Concentration Alcohol Extract (μg/mL) | Compound A (μg/mL) |
|---|---|---|
| KA03 | 100 | 100 |
| KA04 | 100 | 50 |
| KA05 | 100 | 25 |
| KA06 | 200 | 50 |
| KA07 | 100 | 50 |
| ATCC 43504 | 100 | 25 |

The results showed that the lowest minimum inhibitory concentration of 25 μg/mL was obtained by the isolated compound A1 against *H. pylori* strain KA05 and *H. pylori* strain ATCC 43504. However, a MIC of 50 μg/mL was obtained against *H. pylori* strains KA02, KA04, KA06, and KA07, as shown in Table 4.

Accordingly, the *C. pilosellifolius* extract provides a safe and effective method for reducing and inhibiting the incidence of peptic ulcers and the spread of ulcerous tissue. The extract is also effective in treating *H. pylori* infections by reducing and inhibiting the growth or spread of the infection, as evidenced by the disk diffusion tests showing the susceptibility of the bacteria to the abstract. In addition, the active ingredient isolated from the extract and purified has been shown to exhibit an even more potent effect in treating peptic ulcers and *H. pylori* infections than the extract. At present, the cytoprotective mechanism and the anti *H. pylori* activity may explain the potent anti-ulcerogenic activity of the total alcohol extract and active ingredient isolated for the first time from *C. pilosellifolius*. Moreover, the extract was found to be safe and efficacious for use as it showed no signs of acute toxicity and no alteration on liver and kidney functions upon long term use.

It is to be understood that the present invention is not limited to the embodiments described above, but encompasses any and all embodiments within the scope of the following claims.

We claim:

1. A method of treating peptic ulcers and/or gastric disorders resulting from a *Helicobacter pylori* (*H. pylori*) infection in a mammal in need thereof, comprising the step of administering an effective amount of an alcoholic extract of *Convolvulus pilosellifolius* to said mammal, wherein the alcoholic extract comprises an active compound having the formula:

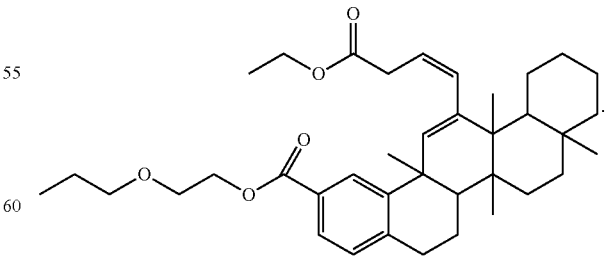

2. The method of claim 1, wherein said step of administering comprises administering the extract orally.

3. The method of treating peptic ulcer of claim 1, where said extract is prepared by a process comprising:

homogenizing *Convolvulus pilosellifolius* aerial plant parts to prepare a homogenized powder;
percolating the powder with an alcoholic solvent to prepare a suspension;
filtering the suspension;
repeating the percolating step to obtain a filtrate; and
isolating the extract from the filtrate.

4. The method of claim 3, wherein said percolating step is performed four times.

5. The method of claim 4, wherein said alcoholic solvent comprises ethanol.

6. A method in a mammal in need thereof, comprising the step of administering an alcoholic extract of *Convolvulus pilosellifolius* to said mammal in an amount effective to reduce and inhibit formation of ulcerous lesions, wherein the alcoholic extract comprises an active compound having the formula:

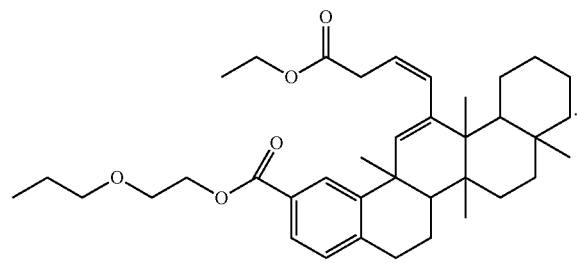 [SMILES: CCCOCCOC(=O)c1ccc2c(c1)C1(C)C=C(/C=C\CC(=O)OCC)C3(C)C4CCCCC4(C)CCC3(C)C1CC2]

7. The method according to claim 6, wherein said effective amount comprises about 500 mg/kg of body weight.

8. A method of treating a *Helicobacter pylori* (*H. pylori*) infection in a mammal in need thereof, comprising the step of administering an alcoholic extract of *Convolvulus pilosellifolius* to said mammal in an amount to inhibit and reduce the *H. pylori* infection, wherein the alcoholic extract comprises an active compound having the formula:

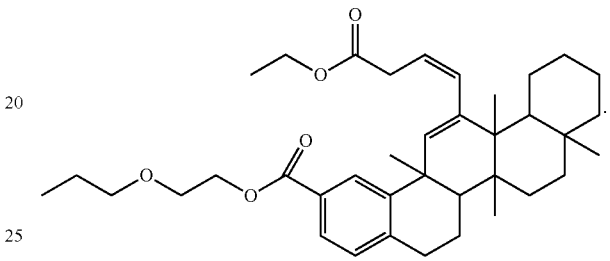

\* \* \* \* \*